(12) United States Patent
Pleil

(10) Patent No.: US 9,750,539 B2
(45) Date of Patent: Sep. 5, 2017

(54) MEDICAL INSTRUMENT

(71) Applicant: Aesculap AG, Tuttlingen (DE)

(72) Inventor: Thomas Pleil, Bad Duerrheim (DE)

(73) Assignee: Aesculap AG, Tuttlingen (DE)

( * ) Notice: Subject to any disclaimer, the term of this patent is extended or adjusted under 35 U.S.C. 154(b) by 429 days.

(21) Appl. No.: 14/479,407

(22) Filed: Sep. 8, 2014

(65) Prior Publication Data
US 2015/0080975 A1   Mar. 19, 2015

(30) Foreign Application Priority Data

Sep. 16, 2013 (DE) .................... 10 2013 110 171

(51) Int. Cl.
*A61B 17/68* (2006.01)
*A61B 17/80* (2006.01)
*A61B 17/88* (2006.01)
*A61B 90/00* (2016.01)

(52) U.S. Cl.
CPC .......... *A61B 17/688* (2013.01); *A61B 17/808* (2013.01); *A61B 17/8863* (2013.01); *A61B 17/8883* (2013.01); *A61B 2090/037* (2016.02)

(58) Field of Classification Search
CPC .................................................. A61B 17/688
See application file for complete search history.

(56) References Cited

U.S. PATENT DOCUMENTS

| | | | |
|---|---|---|---|
| 5,800,436 A | 9/1998 | Lerch | |
| 6,068,631 A | 5/2000 | Lerch | |
| 6,258,091 B1 * | 7/2001 | Sevrain | A61B 17/688 606/213 |
| 6,270,500 B1 | 8/2001 | Lerch | |
| 6,328,743 B2 | 12/2001 | Lerch | |
| 6,589,244 B1 | 7/2003 | Sevrain et al. | |
| 6,685,707 B2 | 2/2004 | Roman et al. | |
| 6,726,688 B2 | 4/2004 | Lerch | |
| 6,755,834 B2 * | 6/2004 | Amis | A61B 17/688 606/104 |
| 6,962,591 B2 | 11/2005 | Lerch | |
| 7,387,633 B2 | 6/2008 | Ahmad et al. | |
| 7,476,241 B2 | 1/2009 | Ahmad et al. | |
| 8,029,552 B2 | 10/2011 | Weinacker et al. | |
| 8,771,322 B2 | 7/2014 | Ahmad et al. | |

(Continued)

FOREIGN PATENT DOCUMENTS

| | | |
|---|---|---|
| DE | 198 32 798 | 11/1999 |
| DE | 297 24 567 | 2/2003 |

(Continued)

*Primary Examiner* — Andrew Yang
(74) *Attorney, Agent, or Firm* — Lipsitz & McAllister, LLC

(57) ABSTRACT

The present invention relates to a medical instrument for applying a bone plate fixing device which comprises a first bone contact element with a rod-shaped connecting member protruding therefrom and defining a longitudinal direction and a second bone contact element which is movable on the connecting member towards the first bone contact element, characterized by a feed apparatus comprising a feed element for application to the second bone contact element, a guide element with a proximal and a distal end for guiding movement of the feed element and a feed mechanism for moving the feed element in the distal direction relative to the guide element.

25 Claims, 10 Drawing Sheets

(56) References Cited

U.S. PATENT DOCUMENTS

| | | |
|---|---|---|
| 2001/0011173 A1 | 8/2001 | Lerch |
| 2002/0004661 A1 | 1/2002 | Sevrain et al. |
| 2002/0040224 A1 | 4/2002 | Lerch |
| 2002/0095156 A1 | 7/2002 | Kuras et al. |
| 2003/0125743 A1 | 7/2003 | Roman et al. |
| 2004/0172029 A1 | 9/2004 | Lerch |
| 2004/0210224 A1 | 10/2004 | Ahmad et al. |
| 2005/0090831 A1 | 4/2005 | Ahmad et al. |
| 2006/0009772 A1 | 1/2006 | Lerch |
| 2008/0275511 A1 | 11/2008 | Weinacker et al. |
| 2009/0093812 A1 | 4/2009 | Ahmad et al. |
| 2010/0305619 A1 | 12/2010 | Knöpfle et al. |

FOREIGN PATENT DOCUMENTS

| | | |
|---|---|---|
| DE | 10 2009 003 177 | 11/2010 |
| EP | 0 920 837 | 3/2004 |
| EP | 1 985 248 | 10/2008 |
| WO | WO 2004/089231 | 10/2004 |

\* cited by examiner

US 9,750,539 B2

MEDICAL INSTRUMENT

CROSS-REFERENCE TO RELATED APPLICATIONS

This application claims the benefit of German application number 10 2013 110 171.2 filed on Sep. 16, 2013, which is incorporated herein by reference in its entirety and for all purposes.

FIELD OF THE INVENTION

The present invention relates to medical instruments for applying a bone plate fixing device generally, and more specifically to a medical instrument for applying a bone plate fixing device which comprises a first bone contact element with a rod-shaped connecting member protruding therefrom and defining a longitudinal direction and a second bone contact element which is movable on the connecting member towards the first bone contact element.

BACKGROUND OF THE INVENTION

A bone plate fixing device of the type described is known for example from EP 0 920 837 B1. With it, it is possible in particular to refix bone plates prepared for opening up a skull simply back on the skull once a surgical operation has been completed. The first bone contact element is applied on the inside of the skull both to the remaining cranial bone and to the bone plate, the connecting member projecting from the saw gap between the bone plate and the remaining cranial bone. To secure the bone plate fixing device, it is known to hold the end of the connecting member projecting from the skull and to slide the second bone contact element towards the skull using forceps until the bone flap and the remaining skull are held clamped between the two bone contact elements. Preferably, three to five bone plate fixing devices are used to fasten the bone flap in the desired manner to the skull.

Application of the bone plate fixing device in the described manner is relatively complex.

SUMMARY OF THE INVENTION

In a first aspect of the invention, a medical instrument for applying a bone plate fixing device comprises a first bone contact element with a rod-shaped connecting member protruding therefrom and defining a longitudinal direction. Said instrument further comprises a second bone contact element which is movable on the connecting member towards the first bone contact element. Said instrument further comprises a feed apparatus with a feed element for application to the second bone contact element, a guide element with a proximal and a distal end for guiding movement of the feed element and a feed mechanism for moving the feed element in the distal direction relative to the guide element.

BRIEF DESCRIPTION OF THE DRAWINGS

The foregoing summary and the following description may be better understood in conjunction with the drawing figures, of which.

DETAILED DESCRIPTION OF THE INVENTION

Figure 1:
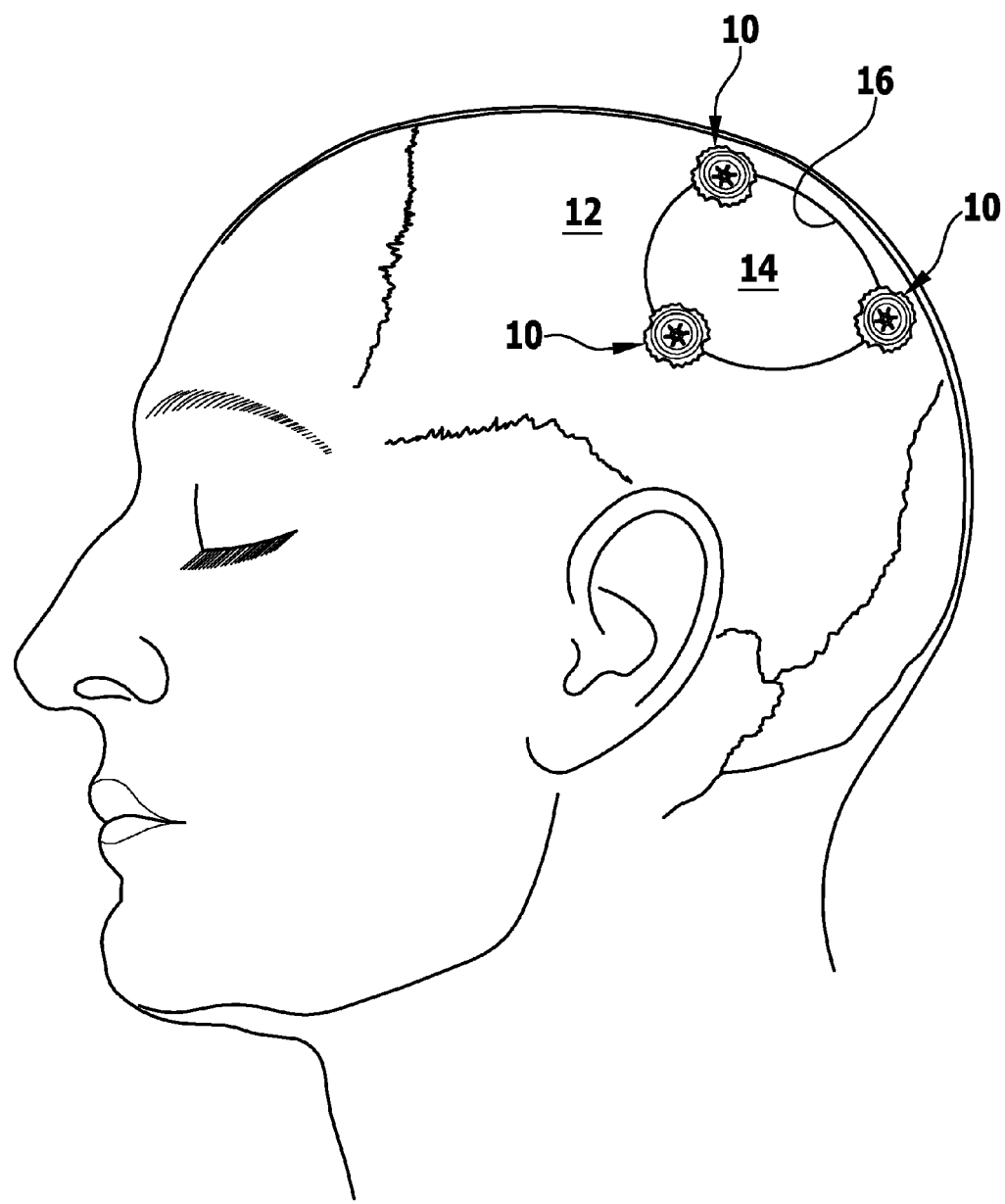
FIG. 1: is a schematic representation of a bone flap fastened with three bone plate fixing devices to a patient's cranial bone.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrument for applying a bone plate fixing device which comprises a first bone contact element with a rod-shaped connecting member protruding therefrom and defining a longitudinal direction and a second bone contact element which is movable on the connecting member towards the first bone contact element, characterised by a feed apparatus comprising a feed element for application to the second bone contact element, a guide element with a proximal and a distal end for guiding movement of the feed element and a feed mechanism for moving the feed element in the distal direction relative to the guide element.

The medical instrument proposed according to the invention in particular makes it possible to apply a bone plate fixing device simply and reliably. Only actuation of the feed mechanism moves the feed element relative to the guide element in the distal direction, wherein movement of the feed element relative to the guide element is guided in defined manner. In particular, a hand or forceps do not need to be used to hold the connecting member of the bone plate fixing device for application purposes. In addition, the instrument may optionally take the form of a disposable instrument, which makes the otherwise conventional cleaning and sterilisation of the instrument superfluous.

It is favourable for the feed mechanism to be configured to convert rotation of one part of the feed apparatus about a longitudinal axis of the instrument into linear advance of the feed element. When, in particular, the longitudinal axis of the instrument is defined on application of the bone plate fixing device by a longitudinal axis of the connecting member, rotation of a part of the feed apparatus, for example a handle, clockwise or counterclockwise may bring about advance of the feed element in the distal direction, such that the second contact element of the bone plate fixing device is moved towards the first contact element. This makes it possible to prevent excessive forces from being exerted on the bone plate fixing device, whereby the bone flap requiring re-fixing or a remaining cranial bone might be damaged.

It is advantageous for the guide element to comprise a sleeve defining a guide element longitudinal axis and at least one first guide member extending in the longitudinal direction of the guide element. The sleeve may be configured in particular in such a way that it surrounds the bone plate fixing device on application and thereby protects it simply and reliably. For example the bone plate fixing device may be inserted immediately after production thereof into the guide element. The guide element thus simultaneously forms a transport container for the bone plate fixing device. The first guide member serves in particular to guide the feed element.

The feed element favourably comprises at least one second guide member co-operating with the at least one first guide member. The two co-operating guide members may predetermine movement of the feed element relative to the guide element in a defined manner.

The instrument can be constructed particularly simply and compactly if the feed element comprises a cylindrical external wall surface and if the at least one second guide member is arranged or formed to protrude radially from the external wall surface. A guide element configured in this way may for example be displaced simply and reliably in a sleeve parallel to the longitudinal axis thereof. Through co-operation of the two guide members, rotation of the feed element relative to the guide element may for example be effected or indeed prevented.

In a particularly simple manner, a guide apparatus comprising the two guide members may be formed if the at least one first guide member takes the form of a guide groove and if the at least one second guide member takes the form of a guide projection corresponding to the guide groove. In this way, the guide projection may in particular protrude into or engage in the guide groove and is guided on movement of the feed element in the distal direction along a path predetermined by the guide groove.

So that the feed element may be translated in defined manner relative to the guide element, but not rotated, it is favourable for the guide groove to take the form of a guide slot extending parallel to the guide element longitudinal axis. The feed element may in this way be translated in linear manner, without rotating in the process.

Sufficiently reliable and defined guidance of the feed element relative to the guide element may be achieved if the instrument comprises two first guide members diametrically opposite one another relative to the guide element longitudinal axis. For example two longitudinal slots extending in parallel may be formed in the sleeve, a guide projection on the feed element protruding into each of them. In this way, the risk of tipping or tilting of the feed element relative to the guide element may be minimised.

Production of the instrument may be further simplified if the feed element is disc-shaped and comprises a connecting member through opening. This makes it possible to slide the feed element over the connecting member, such that it may be applied against the second bone contact element to move the latter towards the first bone contact element.

According to a further preferred embodiment of the invention, provision may be made for the feed apparatus to comprise a drive element which is configured to co-operate with the feed element and as a result of rotation of the drive element relative to the feed element brings about advance thereof in the distal direction. The drive element thus in particular forms part of the drive mechanism for converting a rotational motion into advance of the feed element.

It is favourable for the instrument to comprise a coupling device for movable coupling of the feed element and of the drive element. The coupling device thus in particular defines co-operation of the feed element and of the drive element.

The coupling device can be configured particularly simply, if it comprises at least one first coupling member and at least one second coupling member co-operating with the at least one first coupling member, if the at least one first coupling member is arranged or formed on the feed element and if the at least one second coupling member is arranged or formed on the drive element.

The at least one first coupling member preferably takes the form of a coupling projection and the at least one second coupling member preferably takes the form of a coupling receptacle. The coupling projection is in particular configured and dimensioned such that it may be guided in the coupling receptacle.

A rotational motion can be simply converted into a linear motion if the coupling receptacle takes the form of a spiral drive groove winding around a longitudinal axis of the drive element and open towards the longitudinal axis. In this way, advance of the feed element in the distal direction can be brought about by a rotation of the drive member relative to the feed element, if the latter is secured against rotation.

The stability of the drive mechanism and feed apparatus can be improved if the instrument comprises two first and two second coupling members. In this way it is in particular possible to introduce forces symmetrically and convert them using the drive mechanism.

It may moreover be advantageous for the guide element to have a carrier element which bears the sleeve. The carrier element in particular makes it possible to configure the sleeve in two parts, i.e. for example in the form of two half-shells, which are then each arranged or formed on the carrier element.

The instrument may be particularly simply configured and constructed if the carrier element is symmetrical relative to a mirror plane containing the guide element longitudinal axis.

Favourably, the carrier element has a carrier element opening extending coaxially relative to the guide element longitudinal axis. The carrier element through opening is preferably dimensioned such that the connecting member of the bone plate fixing device passes through it. In this way, the carrier element may not only bear the sleeve but at the same time also form a limit stop acting in the proximal direction for a holding member arranged on the connecting member of the bone plate fixing device. The holding member may be supported on the carrier element if the feed element moves the second bone contact element towards the first bone contact element.

To be able to apply the instrument to the bone plate fixing device in such a way that the carrier element may be applied against the connecting member between a holding member arranged at a proximal end of the connecting member and the second bone contact element, it is favourable for the guide element to have two guide element halves which are connected together in articulated manner. The guide element may be opened in this way, so that the bone plate fixing device may be inserted into the guide element transversely of the longitudinal axis of the connecting member. The articulated joint has in particular the advantage that the two guide element halves may preferably be joined together permanently such that the instrument cannot be broken unintentionally into its individual parts.

The two guide elements are connected together via a hinge defining a pivot axis extending parallel to the guide element longitudinal axis. The guide element may be simply opened by swiveling the two guide element halves relative to one another about the pivot axis.

The hinge may be simply and economically configured if it takes the form of a film hinge. The guide element may thus be formed overall in one piece, for example by injection moulding.

Handling of the instrument can be further improved if it comprises a handle element couplable or coupled to the guide element or the drive element. Such a handle element makes it possible, in particular, to move the guide element and the drive element relative to one another, for example to rotate them relative to one another.

The handle element can be simply coupled to the guide element if the instrument comprises a connecting apparatus for detachable connection of the handle element and the guide element.

Advantageously, the connecting apparatus takes the form of a latching or snap-on connecting apparatus. A latching or snap-on connecting apparatus simplifies assembly of the instrument, since the handle element can be connected to the guide element simply by latching or snapping thereonto.

According to a further preferred embodiment of the invention, it may be provided that the connecting apparatus comprises at least one first connecting member and at least one second connecting member co-operating with the at least one first connecting member and that the at least one first connecting member is arranged or formed on the handle element and that the at least one second connecting member is arranged or formed on the guide element. A connecting apparatus configured in this way allows the handle element and the guide element to be simply and reliably connected together.

Preferably, the at least one first connecting member takes the form of a connecting projection and the at least one second connecting member takes the form of a connecting receptacle. To connect the two elements, it is thus only necessary to engage the connecting member with the connecting receptacle.

It is favourable for the connecting projection to comprise two or more separate latching projections which extend parallel to the guide element longitudinal axis in the distal direction away from the handle element and which each bear a latching lug protruding transversely of a connecting projection longitudinal axis defined by the connecting projection. Such a connecting projection may for example be pushed through into a connecting receptacle in the form of a through opening on the guide element or on the carrier element, wherein the at least two, in particular four, latching projections may be pivoted towards one another on connection and, once the latching lugs have passed through the through opening, may spring back into their original position, such that the latching lugs prevent the connecting projection from being pulled back. This makes it possible to avoid unintentional detachment of the handle element from the guide element.

It is advantageous for the connecting receptacle to take the form of a through opening of the carrier element extending parallel to the guide element longitudinal axis. Thus, the handle element may be connected in the described manner with the carrier element, for example by latching. Furthermore, in this way it may be coupled directly on the proximal side to the carrier element.

A particularly good, reliable and robust connection between the handle element and the guide element may be achieved if two first and two second connecting members are provided, which are arranged or formed symmetrically relative to the guide element longitudinal axis.

Handling of the instrument may be further improved in a simple manner if the handle element comprises two handle wings oriented in the radial direction. These simultaneously form levers which thus define and at the same time limit the maximum torque which can be introduced.

It may moreover be favourable for the handle element to comprise a holding member receptacle which is open in the distal direction. The holding member receptacle in particular makes it possible to receive in a defined manner a holding member held on the connecting member of the bone plate fixing device and retain it therein, if it is for example withdrawn from the connecting member in the event of a predefined withdrawal moment being exceeded. It is thus possible to prevent the holding member from falling out in an undesired manner and in the worst case scenario from being lost in the operation site.

It is advantageous for the holding member receptacle to be closed on the distal side by the carrier element if the handle element is connected to the guide element. In this way, a receiving space can be formed for the holding member, in which the latter may remain if it is detached from the connecting element in the described manner for example in the event of a predefined withdrawal torque being exceeded.

It is favourable for the handle element to comprise a handle element through opening extending coaxially relative to the guide element longitudinal axis. This makes it possible to place the handle element from a proximal direction over the connecting member and optionally the holding member fixed thereto and connect it with the guide element.

To limit relative motion of the guide element and of the drive element in a direction parallel to the guide element longitudinal axis, it is advantageous for the guide element to comprise a limit stop for the drive element to prevent movement of the drive element in the distal direction relative to the guide element. In this way, the guide element and the drive element may be secured relative to one another in the axial direction.

The limit stop may be particularly simply configured if the limit stop takes the form of an annular projection oriented in the radial direction.

The instrument may be configured particularly simply and compactly if the limit stop is arranged or formed on the distal end of the sleeve. In this way, the limit stop may in particular prevent the drive element from being movable in the distal direction relative to the guide element.

It is favourable for the drive element to have a limit stop groove corresponding to the limit stop and oriented in the direction of the guide element longitudinal axis. The limit stop may be received in the limit stop groove in this way, without the limit stop projecting in particular over an outer face defined by the drive element.

It may furthermore be advantageous for the handle element to comprise a connecting member separating opening. This makes it possible in particular to break off the connecting member by simple pivoting to and fro after detachment of the holding member and once the two bone contact elements have adopted their final relative positions, and thus to remove the part of the connecting member projecting from the second bone contact element.

The connecting member separating opening can be produced particularly simply if it takes the form of a bore passing through a handle wing of the handle element. Preferably, the bore extends in such a way that it does not intersect the longitudinal axis defined by the handle element. In this way, the handle element can be gripped reliably if the connecting member is to be separated. This in particular reduces the risk of injuries to the surgeon on separation of the connecting member.

According to a further preferred embodiment of the invention, provision may be made for the instrument to comprise a bone plate fixing device which has a first bone contact element with a rod-shaped connecting member protruding therefrom and defining a longitudinal direction and a second bone contact element which may be moved on the connecting member towards the first bone contact element. The instrument may thus be provided as a unit with the implant in order to simplify application of the bone plate fixing device. Thus, for example, the bone plate fixing device, i.e. the implant, may be assembled and sterilised with the application instrument directly by the manufacturer, such that it may be used directly in a surgical operation. Thus, no further instruments are necessary for handling and applying the bone plate fixing device.

It is favourable for the bone plate fixing device to comprise a holding member which is arranged in clamping manner on a proximal end of the connecting member. It may in principle be connected non-detachably with the connecting member. It is also feasible to connect it with a defined clamping force to the connecting member, in order in this way to predetermine a withdrawal force for detaching the holding member from the connecting member. This is particularly advantageous because in this way it is possible to limit a maximum feed force which may be applied to the feed element to move the bone contact elements towards one another. In other words, force limiting of the instrument may be defined by the defined connection of the holding member and of the connecting member.

It is favourable for the holding member to take the form of a sleeve which comprises a first and a second sleeve portion, which first sleeve portion has a smaller external diameter than the second sleeve portion. In this way, a limit stop may be formed in the transition region from the first sleeve portion to the second sleeve portion. This may in particular prevent the holding member from falling out of the holding member receptacle of the handle element in the proximal direction, if the holding member is separated from the connecting member.

The bone plate fixing device may be of particularly compact construction if the second sleeve portion adjoins the first sleeve portion on the distal side.

The holding member is preferably held on the connecting member with a defined clamping force. This configuration makes it particularly possible, as described, to predetermine force limiting for application of the bone plate fixing device.

It is moreover favourable for the handle element through opening to have an internal diameter conformed to an external diameter of the first sleeve portion. This makes it possible in particular for the first sleeve portion to pass through the handle element through opening but not the second sleeve portion, such that the holding member cannot pass through the handle element in the proximal direction after separation of the connecting member. If the carrier element closes the holding member receptacle on the distal side, the holding member is secured from falling out after detachment from the connecting member in the holding member receptacle.

Moreover, it may be favourable for the holding member receptacle to have an internal diameter conformed to an external diameter of the second sleeve portion. In this way, the second sleeve portion may be received in the holding member receptacle.

At least the second holding member portion may be received substantially completely in the holding member receptacle, if the latter has a depth parallel to the guide element longitudinal axis which corresponds at least to a length of the second sleeve portion parallel to the guide element longitudinal axis.

The instrument can be assembled particularly simply if it comprises a total of four parts. These may in particular be the guide element, the feed element, the drive element and the handle element. These may, as described, be connected together by corresponding latching and snap-on mechanisms, such that no additional tools are required for assembly of the instrument.

The instrument may be particularly simply and inexpensively produced if it is made from one or more plastics. These plastics are preferably sterilisable, in particular gamma- or steam-sterilisable. The different parts of the instrument may in particular be made from different plastics which have different mechanical properties which are particularly advantageous for the different elements of the instrument.

FIG. 1 is a schematic representation of use of a bone plate fixing device 10. Its purpose is to fasten a bone flap 14 removed from a cranial bone 12 back to said cranial bone 12, in order to re-close the hole 16 in the cranial bone 12 opened up when the bone flap 14 was removed.

The bone plate fixing device 10 comprises a first bone contact element 18 which is fastened to a connecting member 20. The first bone contact element 18 forms a distal end of the bone plate fixing device 10. It may optionally be slightly curved and have a serrated edge 22. Furthermore, the bone plate fixing device 10 comprises a second bone contact element 24 which has virtually the same shape as the first bone contact element 18. However, it is arranged in mirror-symmetry to the first bone contact element 18 and has a central through opening 26, from which six slots 28 extend radially towards the edge 30 of the second bone contact element 24. Each pair of slots 28 thus separate short triangular spring flaps 32 from one another, these being oriented towards a longitudinal axis 34 of the bone plate fixing device 10.

Starting from the first bone contact element 18, the connecting member 20 has a retaining portion 36. This comprises a plurality of equidistantly arranged, annular projections 38 which between them define annular grooves 40. The retaining portion 36 is adjoined on the proximal side by a handling portion 42 which extends as far as a proximal end 44 of the bone plate fixing device 10. An external diameter of the handling portion 42 is somewhat smaller than an external diameter of the projections 38. A sleeve-type holding member 46 comprising a first sleeve portion 48 and a second sleeve portion 50 is placed on the proximal end 44 of the connecting member 20. An external diameter of the first sleeve portion 48 is smaller than an external diameter of the second sleeve portion 50.

An annular constriction 52 is additionally formed on the second sleeve portion 50, such that the second sleeve portion 50 is in practice defined by two toroidal projections 54. The holding member 46 is fastened in clamping manner to the connecting member 20, for example by flanging or crimping. In this way, it may be withdrawn from the connecting member 20 in the proximal direction with a defined withdrawal force.

Figure 2:
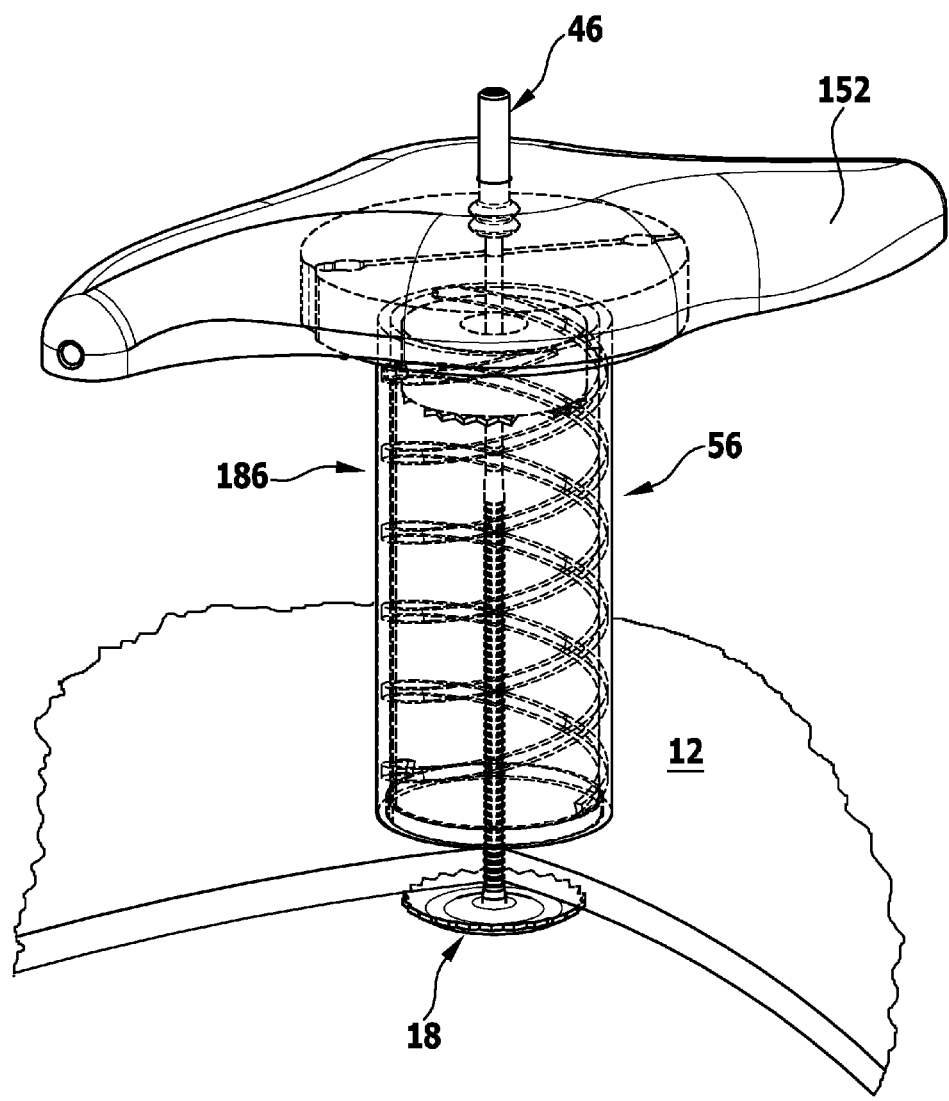
FIG. 2: is a schematic, perspective, partially open overall view of an instrument for applying a bone plate fixing device, on application of the latter to the patient's skull.

To apply the bone plate fixing device 10, a medical instrument is used which is shown schematically in FIG. 2 and is designated overall with reference sign 56. This is hereinafter also designated as an applicator 58. The applicator 58 comprises a total of four parts, namely a feed element 60, a guide element 62, a drive element 64 and a handle element 66. Below, the stated parts are described individually and in their co-operation. The instrument 56 comprises a feed apparatus designated overall with reference sign 186, which feed apparatus comprises the guide element 62, the feed element 60 and a feed mechanism designated overall with the reference sign 180.

Figure 3:
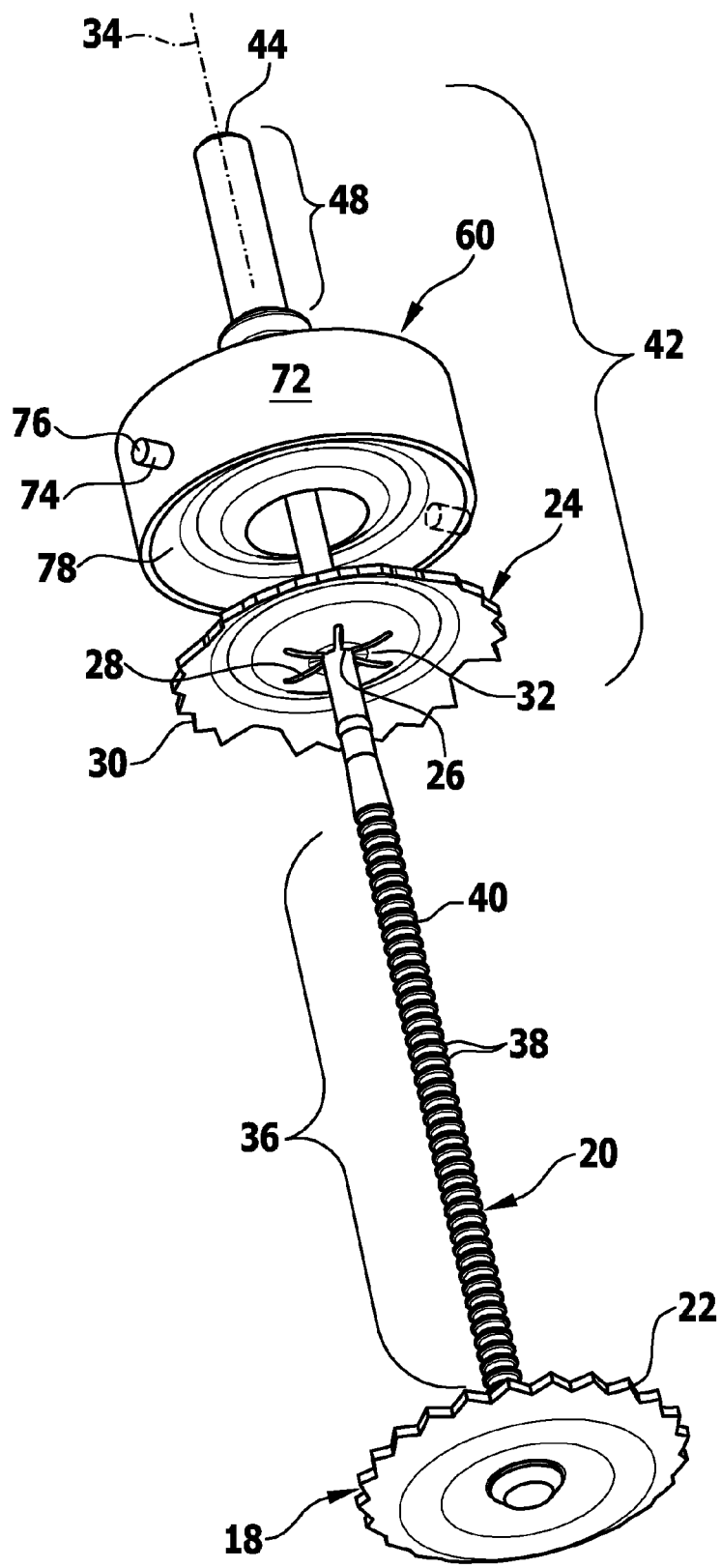
FIG. 3: is a perspective view of the bone plate fixing device with instrument feed element.
Figure 4:
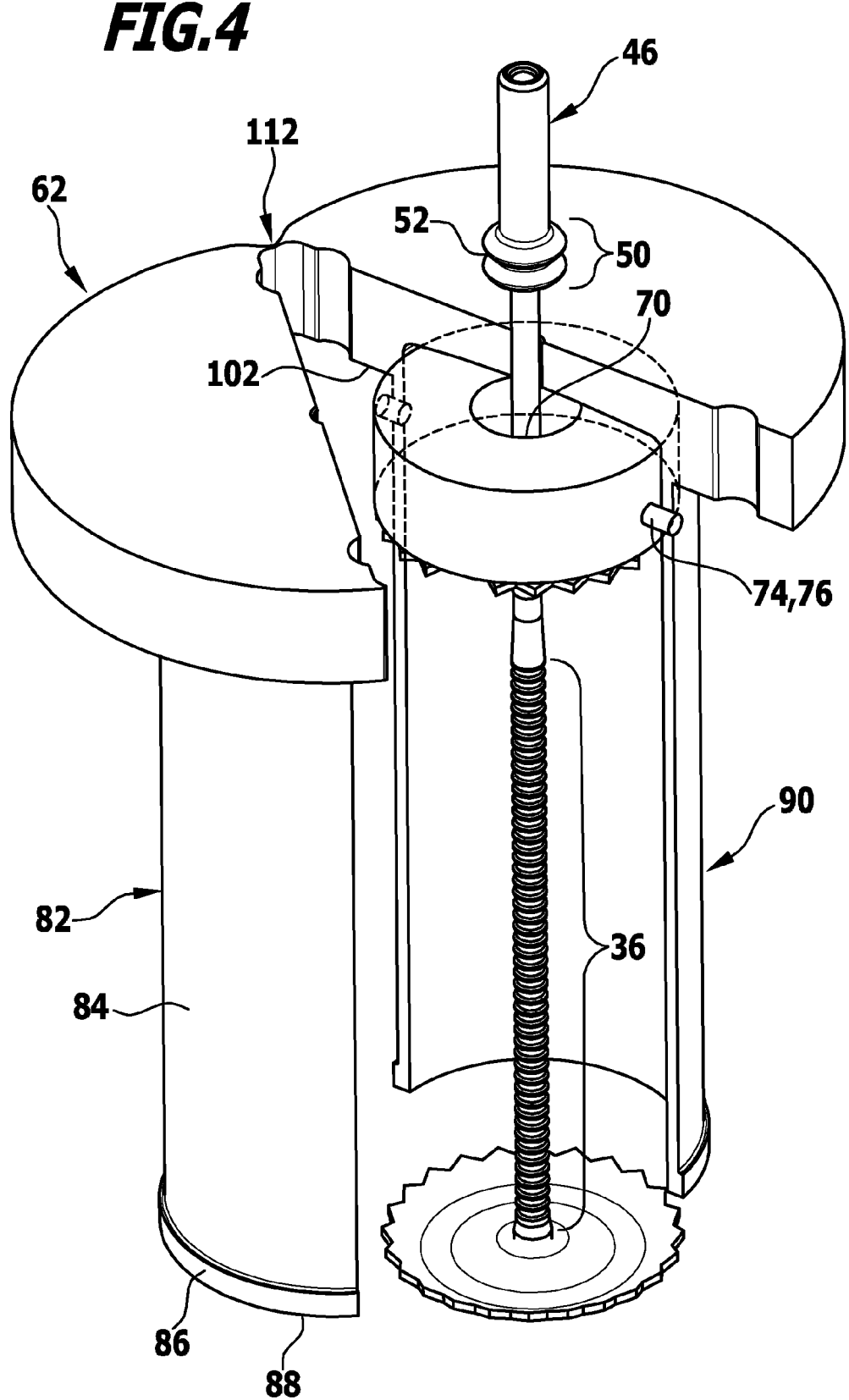
FIG. 4: is a perspective view of the bone plate fixing device with feed element on application of the guide element.

The feed element 60 takes the form of a shallow cylinder 68 comprising a central bore 70, the internal diameter of which is somewhat larger than an external diameter of the second sleeve portion 50, such that the feed element 60 is guided from a proximal direction over the holding member 46 to the first bone contact element 18 and may be brought into contact therewith, as shown schematically in FIGS. 3 and 4.

Two projections 74 pointing radially and diametrically away from one another project from a cylindrical outer wall face 72 of the feed element 60 and form first guide members 76. A bottom 78 of the feed member 60 facing in the distal direction is arched in accordance with an outer surface 80 of the second bone contact element 24 facing in the proximal direction, such that the feed element 60 can be applied substantially snug against the outer surface 80, as illustrated schematically in FIG. 9.

The guide element 62 comprises a sleeve 82, the sleeve wall 84 of which bears a shallow annular projection 86 which faces in a radial direction and is formed directly on the distal end 88 of the sleeve 82. The sleeve wall 84 is thus somewhat thinner on the proximal side of the annular projection 86 and forms a guide portion 90 in this region.

The sleeve 82 defines a guide element longitudinal axis 92. Two slots 94 diametrically opposite one another relative to the guide element longitudinal axis 92 and defining guide grooves 93 divide the sleeve 82 into two sleeve halves 96 symmetrical relative to a mirror plane containing the guide element longitudinal axis 92.

The guide element 62 further comprises a carrier element 98 which takes the form of a shallow cylindrical disc 100. The disc 100 is concentric relative to the guide element longitudinal axis 92 and bears at its bottom 102 the sleeve 82 which protrudes in the distal direction. Starting from the bottom 102, a shallow hollow-cylindrical recess 104 is formed in the disc 100, the internal diameter of which recess corresponds to the internal diameter of the sleeve 82. The disc 100 is moreover provided with a bore 106 coaxial to the guide element longitudinal axis 92. An internal diameter of the bore 106 corresponds to an external diameter of the handling portion 42 of the connecting member 20 in the region on the distal side of the holding member 46 and on the proximal side of the retaining portion 36.

The carrier element 98 is moreover divided by a slot 108 into two carrier element halves 110 symmetrical to one another relative to a mirror plane containing the guide element longitudinal axis 92. The carrier element halves 110 are connected together by a hinge 112. This is arranged at one end of the slot 108. It takes the form of a film hinge and thus allows the two carrier element halves 110 to be pivoted about a pivot axis 116 which extends parallel to the guide element longitudinal axis 92 and is spaced from the disc 100 for instance by half the diameter thereof. The guide element 62 thus comprises two guide element halves 95 which each comprise a carrier element half 110 and a sleeve half 96.

The carrier element 98 furthermore comprises two further bores 118 which are diametrically opposite one another and are arranged relative to the bore 106, specifically in the region of the slot 108. An internal diameter of the bores 118 is somewhat greater than a width of the slot 108.

An internal diameter of the sleeve 82 is conformed to an external diameter of the feed element 60, such that the latter may be displaced inside the sleeve 82 parallel to the guide element longitudinal axis 92. The projections 74 are dimensioned such that they may each engage in one of the slots 94. The slots 94 form second guide members 120 and prevent rotation of the feed element 60 about the guide element longitudinal axis 92. In other words, the feed element 60 can be moved in the sleeve 82 in the distal and proximal directions, but not rotated about the guide element longitudinal axis 92. This is prevented by the projections 74 engaging in the slots 94. The length of the projections 74 in the radial direction is dimensioned such that the first guide members 76 project radially somewhat beyond an external wall surface 122 of the sleeve wall 84.

The drive element 64 likewise takes the form of a sleeve 124. It comprises two coupling receptacles 130 formed in an inner wall surface 126 of a wall 128, these taking the form of spiral drive grooves 132 winding around the guide element longitudinal axis 92 and open towards said axis. The sleeve 124 thus has two helices rotated by 180 degrees relative to one another. The depth of the drive grooves 132 in the radial direction is dimensioned such that the first guide members 76 engage in the drive groove 132.

An internal diameter of the sleeve 124 is conformed to an external diameter of the sleeve 82. Starting from a distal end 134, a limit stop groove 136 open towards the guide element longitudinal axis 92 is formed on the drive element 64. It is moreover open laterally, i.e. facing in the distal direction. The limit stop groove 136 is dimensioned such that it may receive the annular projection 86 forming a limit stop 138. Through the selected dimensions of the sleeves 82 and 124 and owing to the slots 94 provided, the sleeve halves 96 may be moved somewhat towards one another with their distal ends, such that the drive element 64 may be pushed from the distal end in the proximal direction onto the sleeve 82. The sleeve halves 96 give somewhat in the radial direction, as soon as the drive element 64 has been completely pushed on and the portions of the annular projection 86 on the sleeve halves 96 may protrude into the limit stop groove 136. The drive element 64 is secured on the guide element 62 in this way.

The feed element 60 and the drive element 64 are coupled movably together by means of a coupling apparatus designated overall with the reference sign 140. The coupling apparatus comprises first coupling members 142 and second coupling members 144 which co-operate with one another. The first coupling members 142 are arranged or formed on the feed element 60 and the second coupling members 144 on the drive element 64. The first coupling members 142 are formed of coupling projections 146, specifically of the projections 74. These thus form both the first guide members 76 and the first coupling members 142. The second coupling members 144 are formed by the coupling receptacles 130. The feed mechanism 180 comprising the drive element 64 is thus configured to convert rotation of one part of the feed apparatus 186, namely of the guide element 62, about the guide element longitudinal axis 92 into motion of the feed element 60 in the distal direction.

The handle element 66 has a disc-shaped main body 148, away from which two handle wings 150 extend substantially in the radial direction. These are rounded somewhat at the top 152 for ergonomic reasons.

A shallow hollow-cylindrical recess 156 is formed in the main body 148, starting from the bottom 154 of the handle element 66. This has an internal diameter which is conformed to an external diameter of the disc 108. In addition, the handle element has a through opening coaxial to the guide element longitudinal axis, specifically in the form of a handle element through opening 158 which has an internal diameter conformed to an external diameter of the first sleeve portion 148.

The handle element through opening 158 widens out in internal diameter in a single step and thereby forms a holding member receptacle 160 which opens into the recess 156 on the distal side. An internal diameter of the holding member receptacle 160 is conformed to an external diameter of the second sleeve portion 50. Through the selection of the internal diameter of the handle element through opening 158 and holding member receptacle 160, the handle element 66 may be pushed from the proximal side over the holding member 46, to a sufficient extent for the second sleeve portion 50 to come to stop against the step defined between the holding member receptacle 160 and the handle element through opening 158.

To connect the handle element 66 and the guide element 62, a connecting apparatus 162 is provided, which comprises first connecting members 164 and second connecting members 166, which correspond to one another. The first connecting members 164 are arranged or formed on the handle element 66, the second connecting members 166 on the guide element 62. The first connecting members 164 take the form of connecting projections 168, the second connecting members 166 the form of connecting receptacles 170. The connecting projections 168 comprise four separate latching projections 172 which protrude in the distal direction from the recess 156 and in each case bear a latching lug 174 protruding transversely of a connecting projection longitudinal axis defined by the connecting projection 168. The connecting receptacle 170 is formed in each case by a bore 118. The connecting apparatus 162 takes the form of a latching/snap-on connecting apparatus 176.

Figure 6:
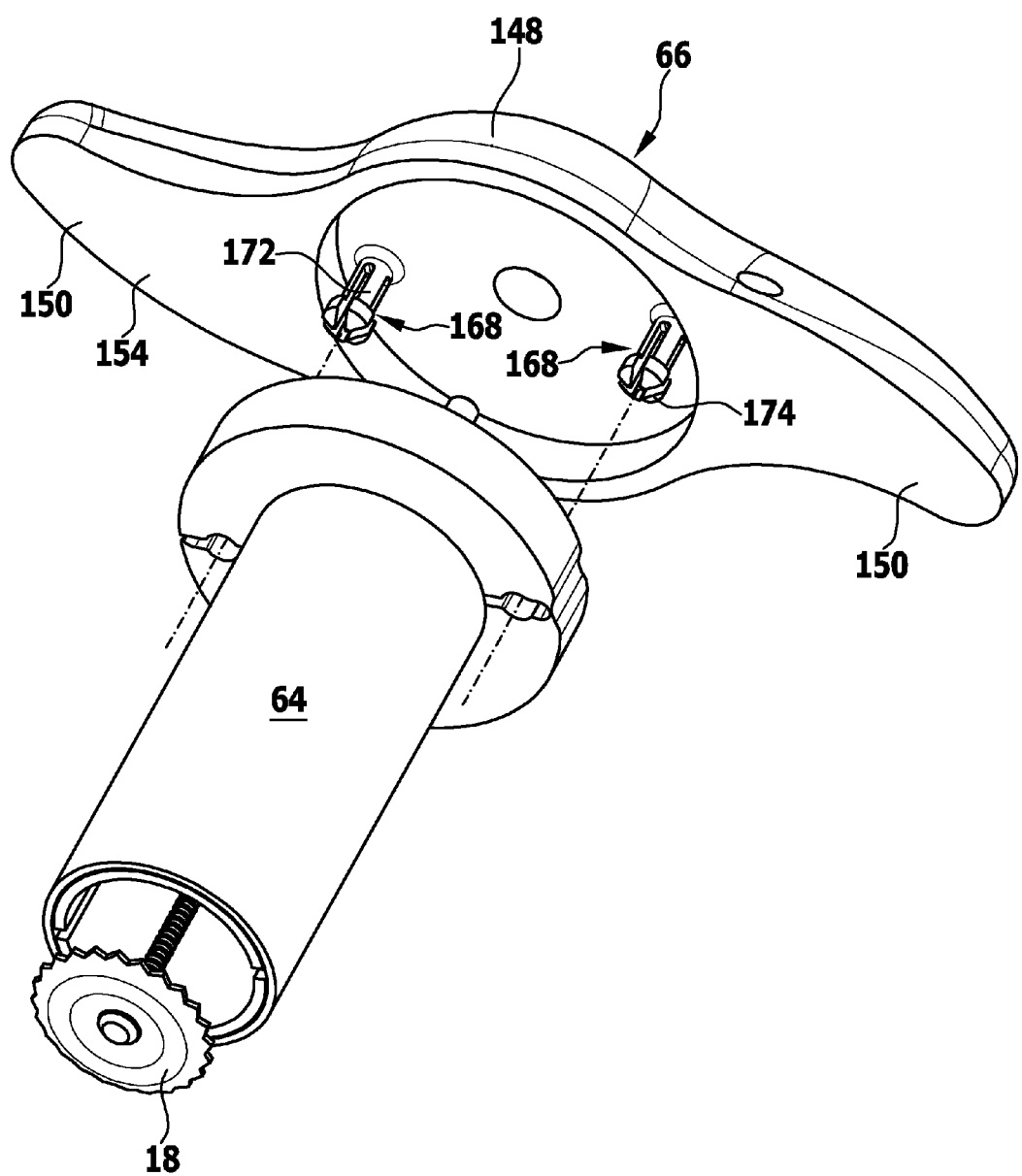
FIG. 6: is a perspective view of the guide element secured with the drive element to the bone plate fixing device prior to positioning of the handle element.

To connect the handle element 66, the latter is pushed in the described manner from the proximal side over the holding member 46, wherein the connecting projections 168 are arranged such that they may be introduced into the bores 118. On introduction, the latching lugs 174 slide along the bores 118, such that the latching projections 174 are each pivoted somewhat towards one another. As soon as the first connecting members 164 have been introduced sufficiently far into the second connecting members 166, the latching lugs 174 may engage behind the bores 118 and the latching projections pivot back out into their original position, as shown schematically in FIG. 6. In this way, the handle element 66 is secured to the guide element 62. The carrier element 68 and the handle element 66 are configured such that the carrier element 98 closes the holding member receptacle 160 on the distal side.

The feed element 60, the guide element 62, the drive element 64 and the handle element 66 are each made in one piece, preferably of a plastics material. This is favourably sterilisable, for example gamma-sterilisable or steam-sterilisable.

The mode of operation of the applicator 58 is described below.

The bone plate fixing device 10 forming an implant is firstly provided in the manner described above, i.e. with the second bone contact element 24 secured to the connecting member 20 on the distal side of the holding member 46. The second bone contact element 24 is initially still located on the proximal side of the retaining portion 36 and is freely movable, in particular translatable, on the handling portion 42 between the second sleeve portion 50 and the retaining portion 36.

The applicator 58 is then brought into engagement with the bone plate fixing device 10 or mounted thereon. In a first step, the feed element 60, as illustrated schematically in FIG. 3, is pushed from the proximal side over the holding member 46, until it rests against the second bone contact element 24. In the next step, the guide element 62 is opened, in particular by pivoting the two guide element halves 95 somewhat apart from one another about the pivot axis 116, as shown schematically in FIG. 4.

Figure 5:
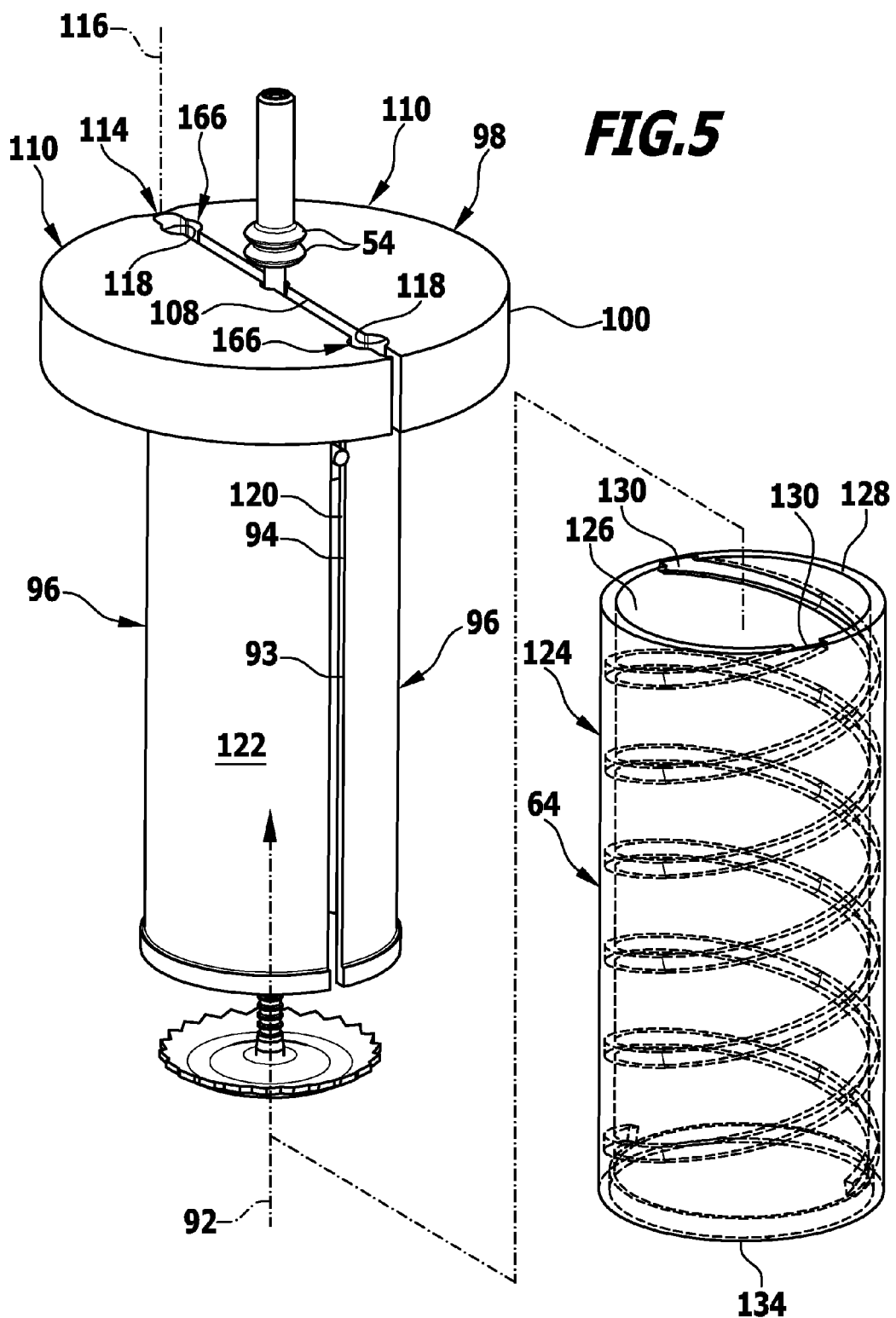
FIG. 5: is a schematic perspective view of the bone plate fixing device with feed element and applied guide element before the drive element is pushed on from a distal direction.

The bone plate fixing device 10 is then inserted with the feed element 16 into the sleeve 82, such that the handling portion 42 passes through the handle element through opening 158 somewhat on the distal side of the second sleeve portion. The first guide members 76 of the feed element 60 are oriented such that they may engage in the second guide members 120. Then the guide element 62 is closed by pivoting the guide element halves 95 towards one another again about the pivot axis 116. The applicator 58 is shown in this position schematically on the left-hand side of FIG. 5.

Then the drive element 64 may be pushed from the distal end in the above-described manner onto the sleeve 82 until the annular projection 86 snaps into the limit stop groove 136. When pushing on the drive element 64, care should be taken to ensure that the first guide members 76, which as described form the first coupling members 142, are able to protrude into the coupling receptacles 130.

Finally, the handle element 66 is placed from the proximal end onto the carrier element 98 and coupled to the guide element 62 by means of the connecting apparatus 162.

Figure 7:
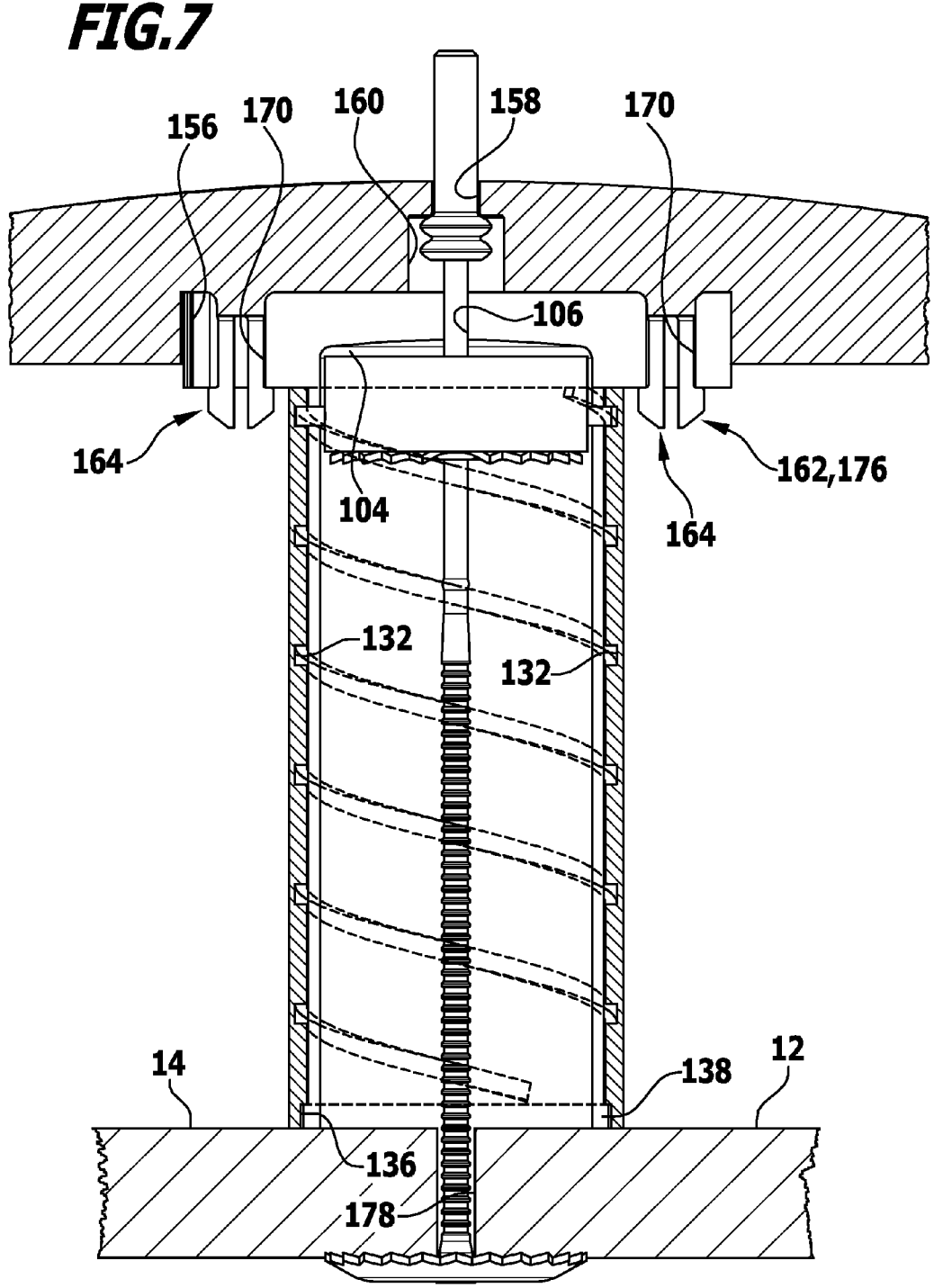
FIG. 7: is a longitudinal sectional view of the instrument with inserted bone plate fixing device after assembly.

The applicator 58 with the bone plate fixing device 10 arranged therein then adopts the position shown schematically in FIG. 7. The first bone contact element 18 may then be inserted under the cranial bone 12 through the hole 16. This may proceed in a similar way with further bone plate fixing devices 10 along one edge of the hole 16. The bone flap 14 is then inserted, such that the connecting members 20 pass through a saw gap 178 produced on removal of the bone flap 14.

Figure 8:
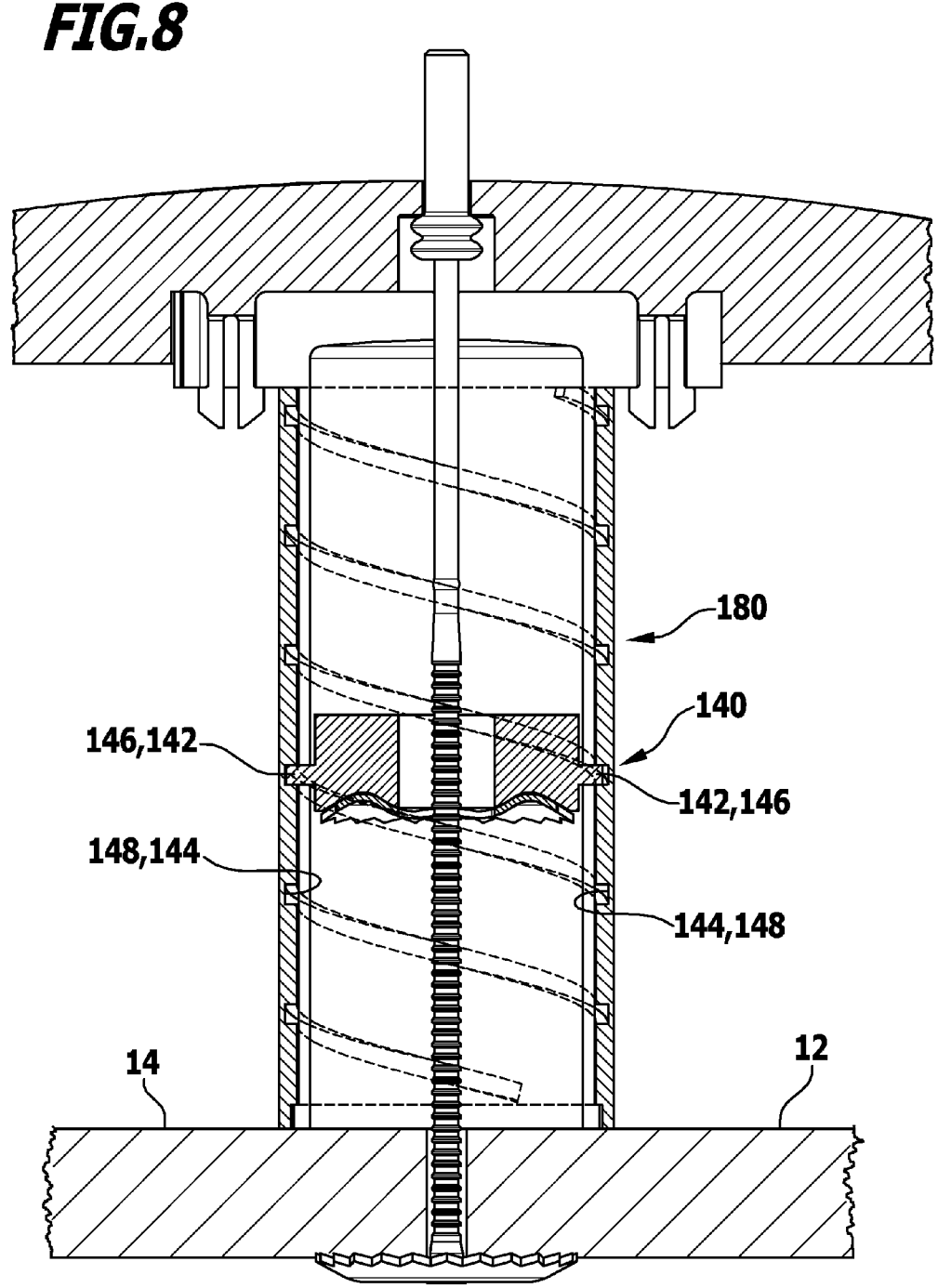
FIG. 8: is a view similar to FIG. 7, but with a feed element already advanced in the distal direction.

A distal end of the drive element 64 then lies on the outside of the cranial bone 12 and of the bone flap 14. If a surgeon holds the drive element 64 firm and turns the handle element 66 clockwise, the guide element 62 and the drive element 64 rotate relative to one another about the guide element longitudinal axis 92. The parts of the instrument 56 which co-operate to form a feed mechanism 180, namely the drive element 64, the guide element 62 and the feed element 60, enforce an advance of the feed element 60 in the distal direction subsequent to the rotation. In the process, the feed element 60 pushes the second bone contact element 24 likewise in the distal direction towards the first bone contact element 18. This advance is shown schematically in FIG. 8.

Figure 9:
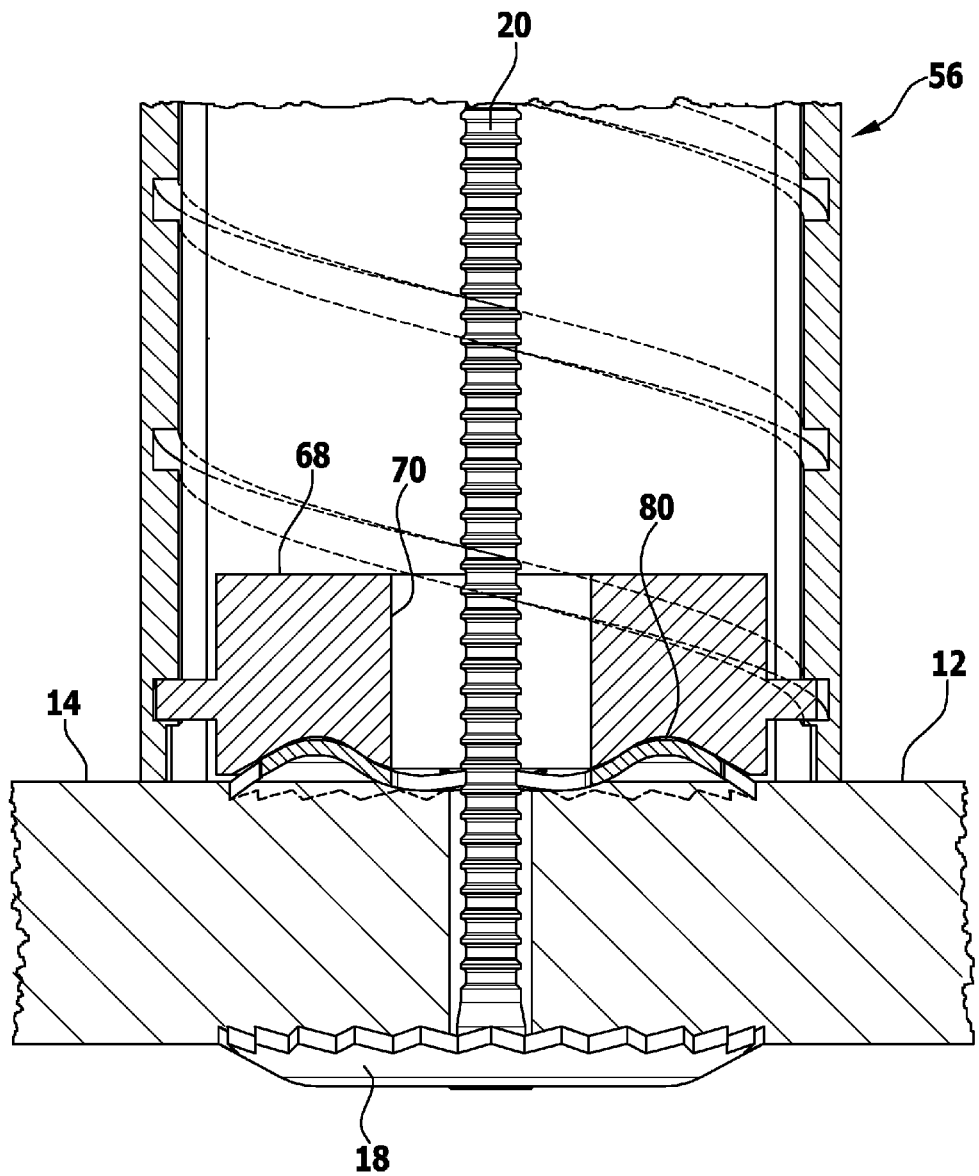
FIG. 9: is an enlarged view of a distal end of the bone plate fixing device after application with the instrument.
Figure 10:
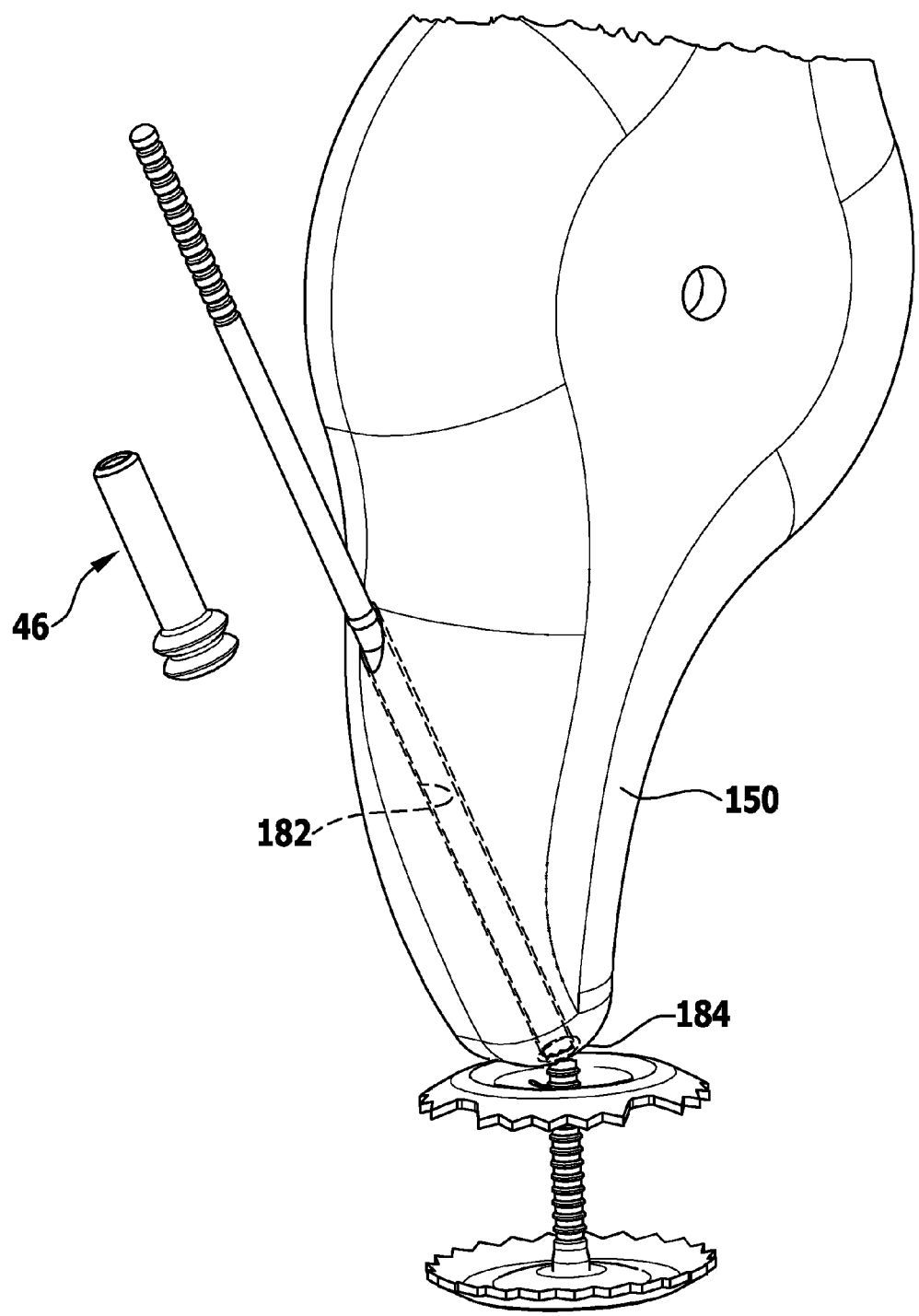
FIG. 10: is a perspective schematic representation of the bone plate fixing device after removal of the holding member from the connecting member on separation of the projecting connecting member with the assistance of the handle element of the instrument by to-and-fro motion.

In the described manner the second bone contact element 24 is advanced until it rests both against the cranial bone 12 and the bone flap 14, as shown schematically in FIG. 9. If the handle element 66 is then turned further in the clockwise direction and the feed force is increased further, the feed force at some point exceeds the clamping force with which the holding member 46 is clamped on the connecting member 20. If this occurs, the holding member 46, which forms an abutment for the guide element 62, becomes detached from the connecting member 20. It cannot however fall out of the applicator 58, since the second sleeve portion 50 of the holding member 46 is secured in the holding member receptacle 160 against falling out.

The applicator 58 can then be withdrawn in the proximal direction from the bone plate fixing device 10.

In a final step, the part of the connecting member 20 projecting above the second bone contact element 24 on the proximal side is additionally separated. One of the two handle wings 150 is provided with a connecting member separating opening extending therethrough. This is dimensioned such that the connecting member 20 can be passed through it. The handle element 66 is brought with a free end 184 of the handle wing 150 having the connecting member separating opening 182 up to the second bone contact element 24. By pivoting to and fro, the connecting member 20 is finally separated.

In the manner described, two, three or even more bone plate fixing devices 10 may be provided, specifically each with their own applicator 58 or as a part thereof, to apply the bone plate fixing devices 10 in the described manner, such that the removed bone flap 14 is ultimately fastened to the cranial bone 12 in the manner illustrated schematically in FIG. 1.

What is claimed is:

1. A medical instrument for applying a bone plate fixing device, the bone plate fixing device comprising a first bone contact element with a rod-shaped connecting member protruding therefrom and defining a longitudinal direction and a second bone contact element which is movable on the connecting member towards the first bone contact element, the medical instrument comprising:
    a feed apparatus comprising:
        a feed element for application to the second bone contact element,
        a guide element with a proximal and a distal end for guiding movement of the feed element, and
        a feed mechanism for moving the feed element in a distal direction relative to the guide element, and
    a handle element couplable or coupled to the guide element or a drive element of the feed mechanism.

2. A medical instrument according to claim 1, wherein the feed mechanism is configured to convert rotation of one part of the feed apparatus about a longitudinal axis of the instrument into a linear feed movement of the feed element.

3. A medical instrument according to claim 1, wherein the handle element comprises at least one of a holding member receptacle which is open in a distal direction and a handle element through opening extending coaxially to a guide element longitudinal axis.

4. A medical instrument according to claim 3, wherein the handle element comprises a connecting member separating opening.

5. A medical instrument for applying a bone plate fixing device, the bone plate fixing device comprising a first bone contact element with a rod-shaped connecting member protruding therefrom and defining a longitudinal direction and a second bone contact element which is movable on the connecting member towards the first bone contact element, the medical instrument comprising:
    a feed apparatus comprising:
        a feed element for application to the second bone contact element,
        a guide element with a proximal end and a distal end for guiding movement of the feed element, and
        a feed mechanism for moving the feed element in a distal direction relative to the guide element,
    wherein:
        the feed element is disc-shaped and comprises a through opening for the connecting member, and,
        the feed mechanism is configured to convert rotation of one part of the feed apparatus about a longitudinal axis of the instrument into a linear feed movement of the feed element.

6. A medical instrument according to claim 5, wherein the guide element comprises a sleeve defining a guide element longitudinal axis and at least one first guide member extending in a longitudinal direction of the guide element.

7. A medical instrument according to claim 6, wherein the feed element comprises at least one second guide member co-operating with the at least one first guide member.

8. A medical instrument according to claim 7, wherein:
    the feed element comprises a cylindrical external wall surface, and
    the at least one second guide member is arranged or formed to protrude away from the external wall surface in a radial direction.

9. A medical instrument according to claim 7, wherein:
    the at least one first guide member takes the form of a guide groove, and
    the at least one second guide member takes the form of a guide projection corresponding to the guide groove.

10. A medical instrument according to claim 9, wherein the guide groove takes the form of a guide slot extending parallel to the guide element longitudinal axis.

11. A medical instrument according to claim 6, wherein the at least one first guide member comprises two first guide members diametrically opposite one another relative to the guide element longitudinal axis.

12. A medical instrument according to claim 6, wherein the guide element comprises a carrier element which carries the sleeve.

13. A medical instrument according to claim 12, wherein the carrier element is symmetrical relative to a mirror plane containing the guide element longitudinal axis.

14. A medical instrument according to claim 12, wherein the carrier element has a carrier element through opening extending coaxially relative to the guide element longitudinal axis.

15. A medical instrument according to claim 5, wherein the feed mechanism comprises a drive element which is configured to co-operate with the feed element and brings about as a result of rotation of the drive element relative to the feed element a feed movement of the feed element in the distal direction.

16. A medical instrument according to claim 15, further comprising a coupling apparatus for movable coupling of the feed element and of the drive element.

17. A medical instrument according to claim 16, wherein:
    the coupling apparatus comprises at least one first coupling member and at least one second coupling member co-operating with the at least one first coupling member,
    the at least one first coupling member is arranged or formed on the feed element, and
    the at least one second coupling member is arranged or formed on the drive element.

18. A medical instrument according to claim 17, wherein the at least one first coupling member takes the form of a coupling projection and the at least one second coupling member takes the form of a coupling receptacle.

19. A medical instrument according to claim 18, wherein the coupling receptacle takes the form of a spiral drive groove winding around a longitudinal axis of the drive element and open towards the longitudinal axis.

20. A medical instrument according to claim 17, wherein:
the at least one first coupling member comprises two first coupling members, and
the at least one second coupling member comprises two second coupling members.

21. A medical instrument according to claim 5, further comprising the bone plate fixing device.

22. A medical instrument according to claim 21, wherein the bone plate fixing device comprises a holding member which is arranged in a clamping manner on a proximal end of the connecting member.

23. A medical instrument for applying a bone plate fixing device, the bone plate fixing device comprising a first bone contact element with a rod-shaped connecting member protruding therefrom and defining a longitudinal direction and a second bone contact element which is movable on the connecting member towards the first bone contact element, the medical instrument comprising:

a feed apparatus comprising:
    a feed element for application to the second bone contact element,
    a guide element with a proximal and a distal end for guiding movement of the feed element, and
    a feed mechanism for moving the feed element in a distal direction relative to the guide element,
wherein the guide element comprises two guide element halves which are connected together in an articulated manner.

24. A medical instrument according to claim 23, wherein the feed element is disc-shaped and comprises a through opening for the connecting member.

25. A medical instrument according to claim 23, wherein the two guide element halves are connected together via a hinge defining a pivot axis extending parallel to a guide element longitudinal axis.

* * * * *